United States Patent [19]

Saragovi et al.

[11] Patent Number: 6,017,878

[45] Date of Patent: Jan. 25, 2000

[54] NERVE GROWTH FACTOR STRUCTURAL ANALOGS AND THEIR USES

[75] Inventors: Uri H. Saragovi, Westmount; Lynne Lesauteur, Rosemére; Claudio A. Cuello, Westmount, all of Canada

[73] Assignee: McGill University, Montreal, Canada

[21] Appl. No.: 08/696,854

[22] PCT Filed: Feb. 7, 1995

[86] PCT No.: PCT/CA95/00059

§ 371 Date: Aug. 7, 1996

§ 102(e) Date: Aug. 7, 1996

[87] PCT Pub. No.: WO95/21193

PCT Pub. Date: Aug. 10, 1995

[30] Foreign Application Priority Data

Feb. 7, 1994 [GB] United Kingdom .................. 9402331

[51] Int. Cl.[7] .............................. A61K 38/12; C07K 7/64
[52] U.S. Cl. ................. 514/9; 530/399; 530/317
[58] Field of Search ..................... 530/399, 317, 530/324–328; 514/9–16

[56] References Cited

U.S. PATENT DOCUMENTS 5,169,764  12/1992  Shooter et al. .

FOREIGN PATENT DOCUMENTS

A-0335637  3/1989  European Pat. Off. .

OTHER PUBLICATIONS

Angeletti, R.H. et al. (1973) *Biochemistry*, 12: 100–115.
Berg, M.M. et al. (1992) *J. Biol. Chem.*, 267:13–16.
Corvera, S. et al. (1989) *J. Biol. Chem.*, 264:12568–12572.
Chao, M. V. (1992) *Neuron*, 9:583–593.
Chothia, C. et al. (1987) *J. Mol. Biol.*, 196:901–917.
Hallbook, F. et al. (1991) *Neuron*, 6:845–858.
Hempstead, B.L. et al. (1991) *Nature*, 350:678–683.
Ibáñez, C.F. et al. (1991) *Eur. Mol. Biol. Org. J.*, 10:2105–2110.
Ibáñez, C.F. et al. (1993) *Eur. Mol. Biol. Org. J.*, 12:2281–2293.
Ip, N.Y. et al. (1993) *Neuron*, 10:137–149.
Itoh et al. (1991) *Cell*, 66:233–243.
Jing, S. et al. (1992) *Neuron*, 9: 1067–1079.
Johnson, D. et al. (1986) *Cell*, 47: 545–554.
Kahle, P. et al. (1992) *J. Biol. Chem.*, 267:22707–22710.
Klein, R. et al. (1991) *Cell*, 65:189–197.
Kremer, N.E. et al. (1991) *J. Cell Biol.*, 115:809–819.
Longo, F. et al. (1990) *Cell Reg.*, 1:189–195.
McDonald, N.Q. et al. (1991) *Nature*, 354: 411–414.
Murphy, R.A. et al. (1993) *J. Neuroscience*, 13(7): 2853–2862.
Rabizadeh, S. et al. (1993) *Science*, 261:345–348.
Saragovi, H.U. et al. (1991) *Science*, 253:792–795.
Saragovi, H.U. et al. (1992) *Biotechnology*, 10: 773–778.
Sibanda, B.L. et al. (1989) *J. Mol. Biol.*, 206: 759–777.
Verdi, J.M. et al. (1994) *Neuron*, 12: 733–745.
Volonté C. et al. (1993) *J. Biol. Chem.*, 268:21410–21415.
Williams et al. (1989) *Proc. Natl. Acad. Sci. USA*, 86:5537.
LeSauteur et al. (1995) *J. Biol. Chem.*, 270: 6564–6569.
Murphy et al. (1993) *J. Neurosciences*, 13(7): 2853–2862.

*Primary Examiner*—Marianne P. Allen
*Attorney, Agent, or Firm*—Klauber & Jackson

[57] ABSTRACT

Cyclic compounds with a 3-dimensional structure that bind at least one neurotrophin receptor (NTR) under physiologic conditions in vitro or in vivo are new. Binding to NTR at least partially mimics or inhibits NT biological activity.

5 Claims, 4 Drawing Sheets

NERVE GROWTH FACTOR STRUCTURAL ANALOGS AND THEIR USES

BACKGROUND OF THE INVENTION (a) Field of the Invention

The invention relates to cyclic compounds having a 3-dimensional structure which binds to neurotrophin receptors, their uses for the treatment or prevention of peripheral and central nervous system diseases, neuromas at the end of an amputated limb and neoplastic diseases which express neurotrophin receptors.

(b) Description of Prior Art

Nerve Growth Factor (NGF) is a protein which has prominent effects on developing sensory and sympathetic neurons of the peripheral nervous system and cholinergic neurons of the CNS. NGF is a polypeptide growth factor member of the neurotrophin family, which includes Brain Derived Neurotrophic Factor (BDNF), Neurotrophin-3 (NT3) and Neurotrophin-4/5 (NT-4/5). NGF controls the survival and development of certain neuronal populations and has been reported to be a mitogen for other cell types. Two cell surface NGF receptors have been characterized on the basis of binding affinity and signal transduction properties, namely the p75 low affinity NGF receptor (LNGFR) and p140 trkA.

The p75 receptor (Kd=$10^{-9}$ M; Johnson, D. et al. (1986) *Cell*, 47: 545–554) is a 75 kDa glycoprotein member of the TNFR/Fas/CD40 family of receptors (Itoh et al., (1991) *Cell*, 66:233–243). p75 contains no intrinsic catalytic activity but can associate with the ERK family of soluble kinases (Volonté C. et al. (1993) *J. Biol. Chem.*, 268:21410–21415), and plays a role in protection from neuronal apoptotic death (Rabizadeh, S. et al. (1993) *Science*, 261:345–348). p75 is also the low affinity binding receptor for BDNF and NT-3 (Ibañez, C. F. et al. (1991) *Eur. Mol. Biol. Org. J.*, 10:2105–2110) but these latter growth factors each have distinct trk receptors.

The p140 trkA receptor is a 140 kDa glycoprotein encoded by the trk proto-oncogene (Klein, R. et al. (1991) *Cell*, 65:189–197). Scatchard analysis of cells expressing only trkA receptors showed a curvilinear plot with Kd ~$10^{-11}$ M and $10^{-9}$ M (Jing, S. et al. (1992) *Neuron*, 9: 1067–1079). The trkA receptor has intrinsic tyrosine kinase activity and is capable of evoking cellular neurotrophic responses in vitro in the absence of p75 LNGFR (Hempstead, B. L. et al. (1991) *Nature*, 350: 678–683).

The co-expression of both p75 and p140 allows detection of a higher affinity NGF receptor and affords a Kd ~$10^{-12}$ M (Jing, S. et al. (1992) *Neuron*, 9: 1067–1079). Hence, p75 can associate with different trk-receptors to form high affinity binding sites but neurotrophin binding specificity is mediated by distinct trk-receptors (Ip, N.Y. et al. (1993) *Neuron*, 10:137–149). The molecular nature of the functional receptor remains unknown.

The NGF protein has been purified, cloned and sequenced (Angeletti, R. H. et al. (1973) *Biochemistry*, 12: 100–115). Cloning of NGF from different species has shown high amino acid sequence homology, and cross-species biological reactivity.

The structure of mouse NGF has been resolved from crystallographic data at 2.3 Å resolution (McDonald, N. Q. et al. (1991) *Nature*, 345: 411–414). In the crystals, the NGF molecule is a tightly associated dimer made up of parallel protomers of 118 amino acids. Each protomer has seven β-strands forming three antiparallel pairs. The β-strands are linked by four exposed regions: three β-turns (termed A'–A", A'''–B, and C–D) and one series of three contiguous reverse-turns (termed B–C).

The β-turn and reverse-turn regions had been noted for their hydrophilic nature and unlike the mostly conserved buried residues of the β-strands the β-turns have little conservation between different neurotrophins (Hallbook, F. et al. (1991) *Neuron*, 6: 845–858). The variability and hydrophilicity of these β-turn regions has prompted the hypothesis that they may be involved in determining neurotrophin receptor specificity because several dimeric molecules use β-turns for critical binding surface(s). Similarly, antibodies and other members of the immunoglobulin gene superfamily (Chothia, C. et al. (1987) *J. Mol. Biol.*, 196:901–917) and other globular proteins (Sibanda, B. L. et al. (1989) *J. Mol. Biol.*, 206: 759–777) use β-turns to interact with complementary sequences with high affinity and specificity.

Experimental evidence using mutagenesis and chimeric molecules has sustained this early hypothesis concerning β-turns of NGF. For example, a chimeric BDNF molecule expressing two β-turns regions of NGF was able to induce neurite outgrowth in NGF responsive sympathetic neurons to the same extent as wild type NGF (Ibañez, C. F. et al. (1991) *Eur. Mol. Biol. Org. J.*, 10:2105–2110).

In spite of the structural information obtained, attempts to create analogs which mimic the activity of NGF β-turns have not been equally successful. Longo et al (Longo, F. et al. (1990) *Cell Reg.*, 1:189–195), found a peptide with sequences from NGF residues 23–35 which inhibited NGF activity. However, this linear peptide did not adopt the β-turn structure from which it was derived in NGF and did not affect the binding of radiolabeled NGF to receptor expressing cells. The peptides were sequence analogs rather than structural analogs of NGF. Furthermore, the concentration of peptide at which inhibition of NGF biological activity occurred (2 mM) was well within concentrations at which non-specific effects can also occur.

Murphy et al (Murphy, R. A. et al. (1993) *J. Neuroscience*, 13(7): 2853–2862) have used a similar approach to study linear peptides derived from NGF comprising amino acids 23–35, 59–67, 69–79, and 91–100. Some limited biological effects were seen for peptides (59–67) and (91–100) in the in vitro assays of neurite survival when suboptimal concentrations of NGF and a 1,000 fold excess of peptide with respect to NGF were used. However, these peptides did not appear to bind the receptors with high affinity and did not compete with radioactive NGF for binding. In addition, antisera raised against the linear peptides did not effectively cross-react with native NGF, further suggesting that the peptides are simply sequence analogs but not true structural analogs of NGF.

The above-mentioned prior studies have contributed to defining important regions of the NGF molecule. However, the exact combination of amino acids of NGF and the 3-dimensional structure(s) that participate in binding to p75 or trkA receptors and cause biological effects remains to be determined.

Frank M. Longo et al. (European Patent Application published under No. EP-A-335,637 on Oct. 4, 1989) have disclosed what are purported to be agonist and antagonist nerve growth factors peptides. These NGF blocking peptides, which are in fact sequence analogs, can be used to inhibit the expression of mRNA and their encoded proteins whose expression is stimulated by NGF. Again, there is no teachings or suggestions of 3-dimensional structures of native NGF or of NGF blocking peptides that participate in binding to p75 or trkA receptors. The linear peptide sequences described by Longo et al. represent synthesized fragments of NGF without teachings or concern with structural motifs, architecture, folding, or bioavailability. The inhibitory activity of these non-structural, linear peptide sequence analogs of NGF was observed at very high, non-pharmacological doses of analog (2 mM), tested versus suboptimal doses of NGF. Further, the inhibitory activity reported did not include an ability to affect either NGF binding, specific receptor binding by NGF, receptor dimerization, neurite extension by NGF responsive cells, or other physiological events associated with NGF function or receptor physiology.

It would be highly desirable to be provided with a cyclic compound having a 3-dimensional structure which binds to neurotrophin receptors, which would mimic the neurotrophin 3-D conformation.

SUMMARY OF THE INVENTION

One aim of the present invention is to provide cyclic compounds having a particular 3-dimensional structure which allows them to be capable of binding to the receptor for neurotrophins, such as NGF, BDNF, NT3 and NT-4/5.

Another aim of the present invention is to provide NGF structural analogs which bind to the NGF receptor.

In accordance with the present invention there is provided a cyclic compound having a 3-dimensional structure which binds to neurotrophin receptors under physiological conditions in vitro or in vivo, and wherein said binding to said receptor at least partially mimics or inhibits said neurotrophins biological activity. The cyclic compound of the present invention may be a structural analogs of NGF or small monomeric, dimeric or polymeric cyclic compounds that mimic the β-turn regions of NGF. Such a cyclic compound includes at least one 3-D conformation selected from a β-turn at region 28–36(A'–A"), 43–49 (A'"–B) and 91–98 (C–D) and three consecutive reserve turns at region 59–65 (B–C). The 3-dimensional conformation of those cyclic compounds may be stabilized by oxidation of cysteine residues to disulfide bridge or by other means of cyclization that do not require Cys, including ionic bonds, salt bridges, Lys-Glu or any chemical bonding.

Also in accordante with the present inventation, the cyclic compounds may be used in vivo as a neurotrophin antagonist to inhibit the neurotrophin binding to its receptor, or to induce the neurotrophin receptor internalization or down-modulation from the surface of cells. Such inhibitions may be used for the treatment of central or peripheral nervous system diseases or for the inhibition or neurite outgrowth in situ in cases of neuromas or for targeting the neurotrophin receptor-expressing tumors.

Also in accordance with the present invention, the cyclic compounds may be used in vivo as neurotrophin agonist to mimic the neurotrophin binding to more then one neurotrophin receptor. Such agonists may be used for the treatment of central nervous system diseases or for peripheral nervous system diseases, or for inducing re-innervation, accelerating cellular differentiation, or inducing terminal differentiation of receptor-expressing tumors.

The following list provides the cyclic compounds in accordance with the present invention, and this is intended to be made without limitation, Z-X C K G K E C X; SEQ ID NO:1
Z-X C D I K G K E C X; SEQ ID NO:2
Z-X C T A I K G K E C X; SEQ ID NO:3
Z-X C I K G K E C X; SEQ ID NO:4
A T D I K G K E V; SEQ ID NO:5
T I G E A D K K V; SEQ ID NO:6
Z-X C I N N S V C X; SEQ ID NO:7
Z-X C N I N N S V C X; SEQ ID NO:8
Z-X C N I N N S C X; SEQ ID NO:9
V N I N N S V F; SEQ ID NO:10
N N S F V I N V; SEQ ID NO:11
Z-X C S N P V E S C X; SEQ ID NO:12
Z-X C A S N P V E S C X; SEQ ID NO:13
X C A S N P V E C; SEQ ID NO:;14
X C A S N P V E C X; SEQ ID NO:15
R A S N P V E S G; SEQ ID NO:16
A N V S R S P E G; SEQ ID NO:17
Z-X C T D E K Q C X; SEQ ID NO:18
Z-X C T D E K Q A C X; SEQ ID NO:19
T T D E K Q A A W; SEQ ID NO:20, and
T E Q A T D K A W; SEQ ID NO:21
  wherein,
  X is any uncharged amino acid or hydropathic amino acid; and
  Z is a absent or a protective group selected from the group consisting of Fmoc group and acetyl groups.

The following list provides the preferred cyclic compounds in accordance with the present invention,
X C K G K E C X; SEQ ID NO:1
X C D I X G E C X; SEQ ID NO:2
X C I K G K E C X; SEQ ID NO:4
X C I N N S V C X; SEQ ID NO:7
X C N I N N S V C X; SEQ ID NO:8
X C N I N N S C X; SEQ ID NO:9
X C S N P V E S C X; SEQ ID NO:12
X C A S N P V E S C X; SEQ ID NO:13
X C A S N P V E C X; SEQ ID NO:15
X C T D E K Q C X; SEQ ID NO:18; and
X C T D E K Q A C X; SEQ ID NO:19.

The cyclic compounds of the present invention are active in various forms, as follows:
  (i) N-terminus can be acetylated or Fmoc protected;
  (ii) next to Cys(C), a Tyr(Y), Phe(F), His(H) or Gly(G) can be added, for example:
    YCTDEKQCY SEQ ID NO:22
    HCTDEKQCH; SEQ ID NO:23
  (iii) some substitutions of the following amino acid side chains are allowed, Asp (D) for Glu (Q) or Glu (Q) for Asp (D) in A'–A" and C–D turns;
  (iv) racemization of amino acids during synthesis or purification is allowed.

Also in accordance with the present invention, the cyclic compounds can be linked to a tracer (metal chelator, radiolabel, biotin or other chemical groups) to follow the fate of the analog in vivo. Also this is useful for imaging or for cytotoxicity of trkA expressing tumors in vivo especially if toxins are linked, or if other therapies are combined.

Also in accordance with the present invention, there in provided a method for the treatment of central nervous system or peripheral nervous systern diseases and neuromas in a patient, which comprises administering an effective amount of a cyclic compound of the present invention to a patient.

Also in accordance with the present invention, there is provided a method for immunization of a mammal against the cyclic compounds of the present invention, which comprises administering by systemic injection an immunizing amount of at least one of the compounds in an immunogenic form in association with a pharmaceutically acceptable carrier.

Also in accordance with the present invention, there is provided a pharmaceutical composition for the treatment of central nervous system diseases and neuromas, which comprises an effective amount of a cyclic compound of the present invention in association with a pharmaceutically acceptable carrier.

Also in accordance with the present invention, there is provided a method for immunization against the structural analogs of the present invention by systemic injection of these compositions in an immunogenic form.

For the purpose of the present invention the following terms are defined below.

The term "neurotrophin" refers to any neurotrophins, such as NGF, BDNF, NT3 and NT-4/5 among others.

The term "neurotrophin receptors" refers to trkA, trkB, trkc, trkE and p75 among others.

"Agonist" refers to a NGF structural analog in accordance with the present invention which binds to a NGF receptor and mimic NGF in that it is capable of at least one biological activity normally associated with NGF.

"Antagonist" refers to a NGF structural analog in accordance with the present invention which binds to a NGF receptor and inhibits at least one biological activity normally associated with NGF.

"Substantial homology" as used herein refers to substantial correspondence between the identity and the sequence of amino acid residues of the native NGF protein and the NGF structural analogs.

The term "effective amount" refers to the amount of NGF structural analogs required to produce a desired agonist or antagonist effect of the neurotrophin biological activity. The precise effective amount will vary with the nature of NGF structural analogs used and may be determined by one of ordinary skill in the art with only routine experimentation.

As used herein, the terms "neurotrophin-mediated activity" or "neurotrophin-associated activity" refers to cellular events triggered by neurotrophin, being of either biochemical or biophysical nature. The following list is provided, without limitation, which discloses some of the known activities associated with neurotrophins, such as NGF: ion flux, phospholipid metabolism, activation of cyclic AMP-dependent protein kinase, activation of cyclic AMP-independent protein kinase and other protein kinases, protein phosphorylation, activation of oncogenic proteins, activation of RNA transcription, stabilization of mRNA species, and enhancement of protein synthesis, receptor stabilization, receptor dimerization or oligomerization, receptor internalization, and eventual protection from cellular apoptosis, induction of growth, and differentiation.

The term "central nervous system diseases" as used herein refer to a disease state in a mammal which includes degenerative growth, development disorders and disorders of the nervous system. Thus diseases characterized by the loss of function and/or degeneration of neurons and nerves. In addition, any disease that can respond to treatment of NGF-responsive or NGF-synthesizing cells with the peptides of the present invention is within the scope of the invention. Exemplary disorders include without limitation, Alzheimer's disease, Down's syndrome, Creutzfeldt-Jacob disease, kuru, Gerstman-Straussler syndrome, scrapie, transmissible mink encephalopathy, Huntington's disease, Riley-Day familial dysautonomia, multiple system atrophy, ALS (amyotropic lateral sclerosis) or Lou Gehrig's disease, Parkinson's disease and the like.

The term "neuromas" as used herein refer to a disease state in a mammal which includes neurite outgrowth or other neural growth of an abnormal sort which causes pain at the end of an amputated limb.

The terms "neoplasmas or tumors" as used herein refer to a disease state in a mammal which includes tumors of neural origin such as neuroblastomas, or non-neural origin such as melanomas, or hematopoietic tumors.

In general, the abbreviations used herein for designating the amino acids are based on the conventional one-letter abbreviations as indicated below:

Alanine A
Arginine R
Asparagine N
Aspartic Acid D
Cysteine C
Glutamine Q
Glutamic Acid E
Glycine G
Histidine H
Isoleucine I
Leucine L
Lysine K
Methionine M
Phenylalanine F
Proline p
Serine S
Threonine T
Tryptophane w
Tyrosine Y
Valine V

DETAILED DESCRIPTION OF THE INVENTION

The cyclic compounds in accordance with one embodiment of the present invention are derived from 3-dimensional domains of NGF which are identified as binding to neurotrophin receptors, such as NGF receptor. Such neurotrophin receptor binding interactions by these compounds cause or prevent neurotrophin biological effects in vivo.

The cyclic compounds in accordance with one embodiment of the present invention include a different β-turn or reverse turn mimic of the NGF. These compounds can be combined dimers or oligomers in any desired combination of the same or different structures to obtain improved affinities and biological effects.

It would be clear to those skilled in the art that this approach can be used to derive neurotrophin receptor binding structures from molecules other than neurotrophins themselves, such as the complementary determining region of antibodies directed against the neurotrophin receptors, or from anti-idiotypic antibodies raised against anti-neurotrophin antibodies (Williams et al. (1989) *Proc. Natl. Acad. Sci. USA*, 86:5537; Saragovi, H. U. et al. (1991) *Science*, 253: 792–795).

In accordance with the present invention, structural NGF analogs were produced by designing structural constraints in the analogs in order to maintain the desired conformation (Saragovi, H. U. et al. (1991) *Science*, 253: 792–795, Saragovi, H. U. et al. (1992) *Biotechnology*, 10: 773–778).

It is demonstrated that cyclic analogs which conserve and closely mimic the three-dimensional structure of the β-turn regions bind to NGF receptors. In contrast, their linear counterparts would seldom adopt the appropriate configuration required to fit the ligand docking site.

Small (average molecular weight ~1,500) structural analogs of β-turns or reverse turns of NGF were designed, synthesized and constrained by cyclization, whereas linear and randomized analogs served as controls. Conformationally constrained analogs had significant NGF antagonistic activity and inhibited NGF mediated neurite outgrowth in p75 LNGFR-p140 trkA expressing PC12 cells grown under optimal conditions. Control linear (not constrained) and randomized sequence analogs did not evidence antagonistic activities at the concentrations tested in the neurite outgrowth assay. Furthermore, some biologically active antagonists were also effective in blocking $^{125}$I-NGF binding to PC12 cells. Furthermore, specific receptor-ligand interactions were mapped by testing the ability of the analogs to inhibit $^{125}$I-NGF binding to p140 trkA receptor expressing fibroblast transfectants.

These data further supports the hypothesis that β-turns are critical in NGF binding to the NGF receptors, and elucidates novel features of receptor-NGF interactions. These data demonstrate that a large macromolecule such as NGF can be reduced to small functional units if the 3-dimensional structure of the native molecule is retained or constrained.

The antagonistic property of the analogs suggests that for agonistic binding the ligand must either engage more than one site on a given receptor, or possess the ability to induce receptor dimerization.

Peptide Synthesis and Characterization

Mouse NGF analogs were synthesized using standard FMOC synthetic procedures. In order to synthesize the large number of analogs required, the Multipin Cleavable Peptide Synthesis System™ (Chiron Mimotopes, Australia) was used. This method allows simultaneous peptide synthesis of 96 peptides on diketopiperazine-linker-derivatized polyethylene pins. Cleavage is performed under mild base conditions using 0.15 M Ammonium bicarbonate pH 8.4. All peptides were synthesized and tested with the amino-termini acetylated and with the Fmoc group intact, and with the diketopiperazine linker present at the carboxy terminus. For cyclization, $NH_3$—X—Cys and Cys—X—$COO^-$ were added to the termini of the indicated peptides, where X can represent any uncharged or hydropathic amino acid (e.g. Gly when Fmoc-amino termini were present, or Tyr or His when it was absent (see Table I)). Following cleavage the peptides were cyclized by oxidation of the Cysteine residues as described by Saragovi et al. (Saragovi, H. U. et al. (1992) *Biotechnology*, 10: 773–778). Cyclization efficiency was determined by the Ellman's procedure to be greater than 70%. Peptides were lyophilized, resuspended in water and purified to greater than 85% in a Waters™ HPLC (0.1% trifluoroacetic acid, 40 min 10–40% acetonitrile (ACN) gradient) using a Vydac™ 218TP C18 (1×25 cm) column. Peptides were characterized by aminoacid analysis (Beckman Model 6300 Analyzer™) and by Mass Spectrometry (SCIEX API III™).

Cell Cultures

All cells were cultured as described. PC12 pheochromocytoma cells expressing rat p140 trkA and p75 LNGFR (American Type Culture Collection, 7th edition, 1992, Catalog of cell lines and hybridomas, R. Hay Editor, accession No. CRL 1721) were grown in DMEM supplemented with 20% Fetal Bovine Serum (FBS), 10% Horse serum, and antibiotics. PC12 cells used for experiments were grown on collagen coated dishes. The NIH-3T3 fibroblast transfectants R7 (p75 and trkA double transfectant) and E25 (trkA transfectant) (Jing, S. et al. (1992) *Neuron*, 9: 1067–1079; kindly provided by Dr. Mariano Barbacid, Bristol-Meyers-Squibb, NJ) were grown in RPMI media supplemented with 5% FBS and antibiotics and the appropriate drug selection.

Neurite Outgrowth Assay

Analogs were tested for their ability to affect NGF induced neurite outgrowth in PC12 cells. PC12 cells were incubated in complete media containing optimal concentrations of NGF (50 ng/ml; approximately 2.0 nM) or basic Fibroblast Growth Factor (bFGF) (50 ng/ml) (Prince Labs, Toronto). NGF analogs or control analogs were then added to a final concentration of 10 $\mu$M, cells were incubated and neurite outgrowth was measured every 24 hrs. for three days. Cells without growth factor added served as baseline, whereas cells with growth factor but without analog added were used for maximum neurite outgrowth determination. All analogs were tested in at least three separate assays from three different synthesis. Samples were coded and analysis were performed blind.

NGF Binding Studies

Analogs were tested for their ability to affect binding of $^{125}$I-NGF (73.1 $\mu$Ci/$\mu$g NEN, DuPont). 0.4–1×10$^6$ cells were incubated in binding buffer (HBSS, 1% BSA, 0.05% Na Azide, pH 7.4) at 4° C. with the indicated concentration of cyclic NGF analogs, control analogs, a titration of unlabeled NGF, or nothing. After 15 min, $^{125}$I-NGF was added to a final concentration of 0.4–2 nM (~40,000 cpm) and the mixtures were further incubated for 40 min at 4° C. Cells were then washed in binding buffer, pelleted, and cell-associated $^{125}$I-NGF was determined. Background binding was measured by the addition of ~2000 fold excess unlabeled NGF, which resulted in less than 10% of maximum binding; or by measuring binding to NGF receptor negative NIH3T3 cells (~5%). Assays were performed >4 times, each from at least three different synthesis (inhibitory analogs) or 1–3 times each from 2 different synthesis (non-inhibitory analogs). Receptor saturation experiments were similarly performed with increasing concentrations of $^{125}$I-NGF ligand and a constant dose of inhibitor.

Design and Synthesis of NGF Analogs.

Four regions of the NGF primary sequence were defined which differ significantly from the primary sequence of other neurotrophins, corresponding to amino acid numbers 28–36 (β-turn A'–A"), 42–49 (β-turn A'''–B), 59–67 (turn B–C), and 91–99 (β-turn C–D) of mouse NGF (Table I). Cyclic peptides (C) were synthesized, and for each a linear (unconstrained sequence) (L) control and a scrambled (randomized sequences) (R) control were also made.

The effect of the analogs on NGF dependent neurite outgrowth were determined. Cells were incubated with 50 ng/ml NGF (A, C, E, G) or with 50 ng/ml bFGF (B, D, F, H). The indicated NGF analogs were added at ~10 μM. Representative results for 3 different analogs are shown. For a summary and complete list of the results from these biological tests see Table II.

TABLE I

NGF Derived Structural Analogs

| REGION | NFG SEQUENCE | ORIGINAL STRUCTURE/ AMINO ACID RESIDUES | ANALOG CODE |
|---|---|---|---|
| A'–A" | Fmoc-X C K G K E C X | β turn 32–35 | C(32–35) (SEQ ID NO: 1) |
| | Fmoc-X C D I K G K E C X | β turn 30–35 | C(30–35) (SEQ ID NO: 2) |
| | Fmoc-X C T A I K G K E C X | β turn 29–35 (ΔD30A) | C(29–35ΔD30A) (SEQ ID NO: 3) |
| | Fmoc-X C I K G K E C X | β turn 31–35 | C(31–35) (SEQ ID NO: 4) |
| | A T D I K G K E V | linear 28–36 | L(28–36) (SEQ ID NO: 5) |
| | T I G E A D K K V | randomized 28–36 | R(28–36) (SEQ ID NO: 6) |
| A'''–B | Fmoc-X C I N N S V C X | β turn 44–48 | C(44–48) (SEQ ID NO: 7) |
| | Fmoc-X C N I N N S V C X | β turn 43–48 | C(43–48) (SEQ ID NO: 8) |
| | Fmoc-X C N I N N S C X | β turn 43–47 | C(43–47) (SEQ ID NO: 9) |
| | V N I N N S V F | linear 42–49 | L(42–49) (SEQ ID NO: 10) |
| | N N S F V I N V | randomized 42–49 | R(42–49) (SEQ ID NO: 11) |
| B–C | Fmoc-X C S N P V E S C X | reverse turn 61–66 | C(61–66) (SEQ ID NO: 12) |
| | Fmoc-X C A S N P V E S C X | reverse turn 60–66 | C(60–66) (SEQ ID NO: 13) |
| | X C A S N P V E C | reverse turn 60–65 | C(60–65) (SEQ ID NO: 14) |
| | R A S N P V E S G | linear 59–67 | L(59–67) (SEQ ID NO: 16) |
| | A N V S R S P E G | randomized 59–67 | R(59–67) (SEQ ID NO: 17) |
| C–D | Fmoc-X C T D E K Q C X | β turn 92–96 | C(92–96) (SEQ ID NO: 18) |
| | Fmoc-X C T D E K Q A C X | β turn 92–97 | C(92–97) (SEQ ID NO: 19) |
| | T T D E K Q A A W | linear 91–99 | L(91–99) (SEQ ID NO: 20) |
| | T E Q A T D K A W | randomized 91–99 | R(91–99) (SEQ ID NO: 21) |

X is any uncharged amino acid or hydropathic amino acid and Fmoc in the protective group used during synthesis.

The indicated sequences (shown from amino to carboxy ends) were synthesized and purified. Cysteine residues not found in the NGF sequences selected were incoporated in the peptides to constrain their conformation by intramolecular disulfide bridging. In some cases other designed modifications of the original NGF sequences were necessary to improve analog solubility and to prevent intermolecular disulfide bridging. For cyclic analogs other designed modifications of the original NGF sequences were done. C=cyclic, L=linear, R=randomized. ΔD30A is an Alanine substitution for Aspartic acid at position 30.

Crystallographic data and modeling of NGF has shown that the conformation of regions 28–36, 43–49, and 91–98 is a β-turns while that of region 59–65 are 3 consecutive reverse turns. In some of our peptides the conformation predicted to exist in NGF was preserved by cyclization, which forces the peptide into a β-turn mimic (Williams et al. (1989) *Proc. Natl. Acad. Sci. USA*, 86:5537). Cyclization was achieved by introducing Cysteine (Cys) residues in the appropriate positions and subjecting the analogs to oxidation. Oxidation of Cys results in a covalent disulfide bridge which stabilizes the desired conformation. All active peptides were purified by HPLC and characterized by ion spray mass spectrophotometry and amino acid analysis.

Inhibition of NGF Function in Biological Assays

Rat PC12 pheochromocytoma cells in culture can differentiate and produce neurites in response to NGF or bFGF. None of the analogs were able to induce neurite projections when added to PC12 cell cultures, suggesting that by themselves they lacked NGF agonistic activity at the concentrations used in these assays.

Two of the inhibitory cyclic analogs, C(32–35), and C(44–48) caused enlargement of the cell size and clumping (Table II). However, non-inhibitory analogs L(42–49), and R(59–67) caused a similar effect, suggesting that this was unrelated to activity.

TABLE II

Bioactivity Of NGF Structural Analogs

| NGF ANALOG | TURN REGION OF NGF | INHIBITION OF NEURITE OUTGROWTH (1) | CHANGES IN CELL SIZE OR APPEARANCE |
|---|---|---|---|
| C(32–35) | A'–A" | ++ | LARGER SIZE |
| C(30–35) | | +± | NONE |
| C(31–35) | | ++ | NONE |
| L(28–36) | | ± | NONE |
| R(28–36) | | ± | NONE |
| C(44–48) | A'''–B | +++ | LARGER/ROUNDING |
| C(43–48) | | +++ | NONE |
| C(43–47) | | + | NONE |
| L(42–49) | | +± | LARGER/ROUNDING |
| R(42–49) | | + | NONE |
| C(60–66) | B–C | ++ | NONE |
| C(60–65) | | ++ | NONE |
| L(59–67) | | + | NONE |
| R(59–67) | | + | LARGER SIZE |
| C(92–96) | C–D | +++± | NONE |
| C(92–97) | | +++ | NONE |
| L(91–99) | | + | NONE |
| R(91–99) | | ± | NONE |

++++ equivalent to 0 ng/ml NGF (complete inhibition)
+++ equivalent to 6.25 ng/ml NGF
++ equivalent to 12.5 ng/ml NGF

TABLE II-continued

Bioactivity Of NGF Structural Analogs

| NGF ANALOG | TURN REGION OF NGF | INHIBITION OF NEURITE OUTGROWTH (1) | CHANGES IN CELL SIZE OR APPEARANCE |
|---|---|---|---|

+ equivalent to 25 ng/ml NGF
− equivalent to 50 ng/ml NGF (no inhibition).

Figure 1:
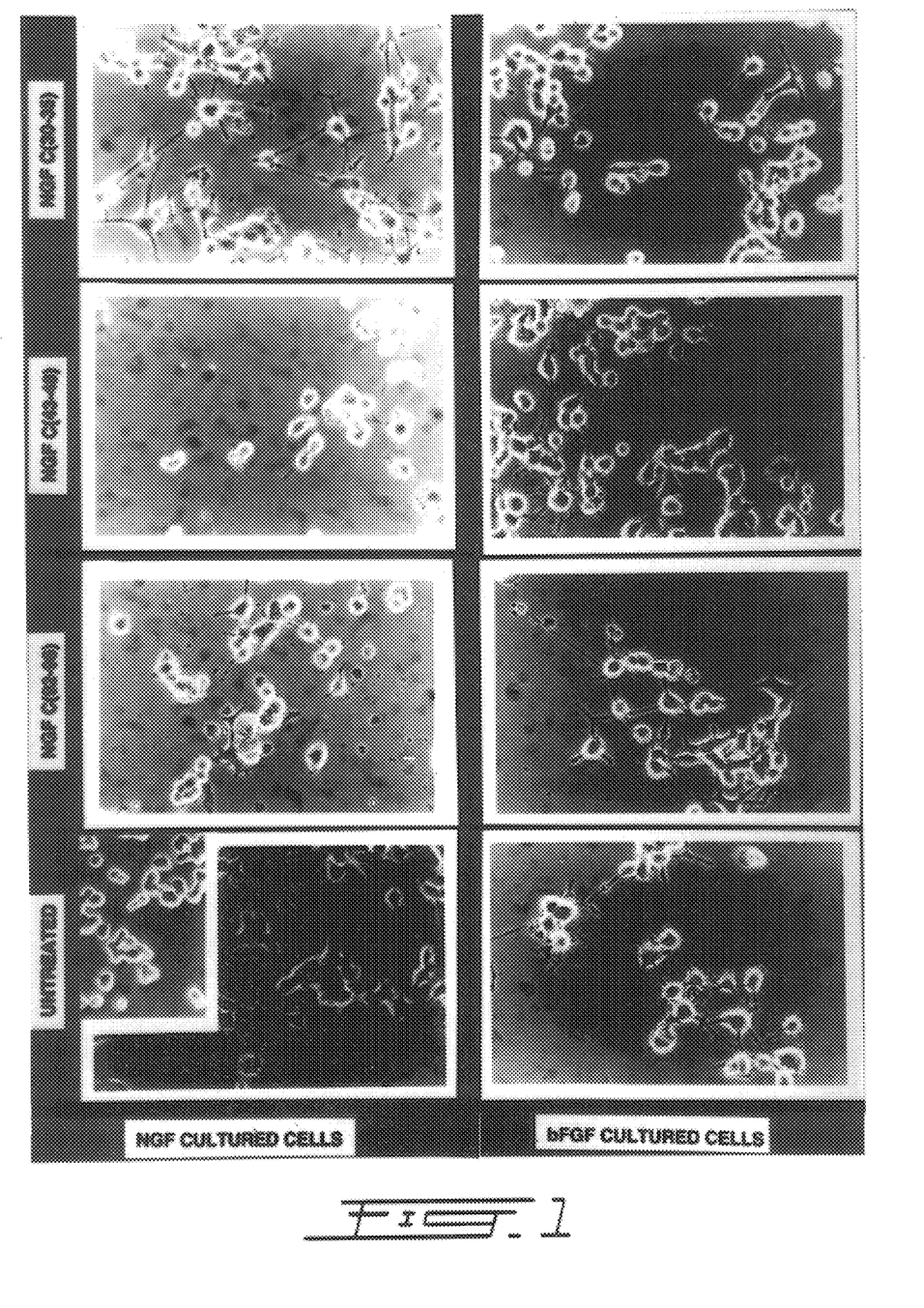
FIG. 1 illustrates the antagonistic bioactivity of the NGF structural analogs in accordance with the present invention.

The analogs were assayed as described for FIG. 1, and NGF mediated PC12 neurite outgrowth measured. The arbitrary units indicating antagonistic activity are the result of direct comparisons with NGF dose response curves done in parallel. Significant inhibition is indicated by +++.

Cyclic analogs C(92–96) and C(92–97) derived from β-turn C–D, and C(43–48) and C(44–48) derived from β-turn A'''–B of NGF demonstrated antagonistic activity and significantly inhibited NGF mediated PC12 cell neurite projections (FIG. 1, C, E), but did not affect bFGF mediated responses (FIG. 1, D, F). In contrast, other cyclic analogs (e.g. β-turn A'–A" analog C(30–35); FIG. 1, G and H) and the linear or randomized analogs did not affect either NGF or bFGF mediated neurite outgrowth (for a summary see Table II).

Controls ruled out toxicity and demonstrated the specificity of the analogs as antagonists of NGF. First, no cell death was observed after culture with the compounds (exceptions which did cause necrosis were C(29-35ΔD30A) from β-turn A'–A" and C(61–66) from β-turn B–C, and were not used further). Second, when the analogs were removed PC12 cells responded normally to NGF. Third, and most importantly, the NGF analogs did not affect PC12 cell neurite outgrowth in response to bFGF suggesting that the analogs were specific for NGF receptors.

The data presented is the first direct demonstration of the involvement of a defined β-turn region of a polypeptide ligand in binding to a defined neurotrophin receptor. Overall, these data provide support for the notion that β-turn regions are crucial for certain ligand-receptor interactions and this concept may now be applied to other members of the neurotrophin family.

This concept is acceptable to the family of neurotrophins because they are highly related in primary sequence and in structure, and their receptors are also highly related. The neurotrophin ligands differ mostly in their β-turns suggesting that specificity of receptor binding is mediated by β-turns. Replication of this invention with the structure of other neurotrophins would be evident to those skilled in the art.

Direct Inhibition of NGF Binding

To determine the mechanism of biological antagonistic activity by the cyclic analogs, $^{125}$I-NGF binding measurements were performed with cell lines expressing both p75 and trkA receptors (PC12 cells and R7 transfectants) or only trkA receptors (E25 transfectants) (Table III). Analogs were used at a concentration of ~40 μM.

Analogs from the C–D β-turn region were effective in inhibiting $^{125}$I-NGF binding to E25, R7 and PC12 cells. Inhibition of binding was roughly comparable to that obtained with 0.1 μM unlabeled NGF (Table III). These analogs were more efficient at inhibiting NGF binding to E25 cells than to R7 cells. Furthermore, while analogs C(92–96) and C(92–97) inhibited NGF binding to E25 cells to a similar degree (71.3% and 64.9% respectively); C(92–96) was more effective than C(92–97) in blocking NGF binding to R7 cells (51.1% versus 24.3% respectively).

TABLE III

INHIBITION OF $^{125}$I-NGF BINDING TO NGF RECEPTORS BY NGF STRUCTURAL ANALOGS

| | % INHIBITION | | |
|---|---|---|---|
| INHIBITOR | PC12 (trkA-p75) | R7 (trkA-p75) | E25 (trkA) |
| 0.1 uM NGF | 69.5 ± 4.5 | 80.0 ± 18.9 | 93.3 ± 8.1 |
| C(92–96) | 86.4 ± 10.4 | 51.1 ± 0.7 | 71.3 ± 13.5 |
| C(92–97) | N.T. | 24.3 ± 9.2 | 64.9 ± 12.4 |
| C(30–35) | N.T. | 0.44 ± 0.6 | 51.1 ± 0.7 |
| C(32–45) | 9.0 (*) | −4.5 ± 6.5 | 30.7 ± 10.5 |
| C(44–48) | N.T. | N.T. | −12.5 ± 5.4 |
| C(43–48) | N.T. | 5.0 (*) | −2.7 ± 8.5 |
| L(91–99) | N.T. | 3.8 ± 1.0 | 2.1 ± 8.5 |
| L(28–36) | 5.0 (*) | −11.3 (*) | 6.4 ± 12.4 |
| L(42–49) | N.T. | 8.0 (*) | −16.0 ± 15.1 |
| L(59–67) | N.T. | N.T. | −9.5 ± 7.5 |

The NGF analogs (~40 μM) were tested singly for their ability to inhibit $^{125}$I-NGF binding to NGF receptor expressing cells. Data shown represents an average percent inhibition of binding ±2 standard errors of the mean (2 SEM). Background binding was determined by adding 2000 fold excess unlabelled NGF. n=>4 (inhibitory analogs), or 1–3 (non-inhibitory analogs). NT=not tested. (*) assayed only once.

Percent inhibition was determined by applying the following formula:

$$1 - \frac{(\text{test binding} - \text{background binding})}{(\text{maximum binding} - \text{background binding})} \times 100\%$$

Analogs C(30–35) and C(32–35) derived from β-turn A'–A" region inhibited NGF binding to E25 cells (albeit less efficiently than the C–D region analogs), but did not affect NGF binding to R7 cells. This may suggest that the A'–A" region binds to trkA receptors which are not in association with p75, or that p75 association to trkA changes the conformation of trkA such that the binding site for the analog is not available or stable.

None of the other cyclic, linear or randomized analogs had significant effects in $^{125}$I-NGF binding (e.g. C(43–48) or L(91–99), Table III). Note that two biologically active cyclic analogs (A'''–B region analogs C(43–48) and C(44–48), Table II) did not inhibit $^{125}$I-NGF binding in these assays and they may function through a different mechanism.

Analogs derived from β-turn A'–A" region also inhibited NGF binding to trkA-expressing E25 cells, albeit with lower potency than the C–D region β-turn analogs. We have not yet measured the IC50 of A'–A" region analogs, but we expect them to be of lower affinity. A'–A" region analogs did not affect NGF binding to p75/trkA expressing cells at all, suggesting that they only bind trkA receptors which are not in association with p75.

Lack of inhibition by A'–A" region analogs on cells expressing both p75 and trkA can be the result of higher receptor affinity for the ligand. Additionally, a receptor conformational change or masking of the docking site can occur upon heterodimerization of p75 and trkA (Verdi, J. M. et al. (1994) *Neuron*, 12: 733–745). Theoretical models of functional NGF receptors (Chao, M. V. (1992) *Neuron*, 9:583–593; Klein, R. et al. (1991) *Cell*, 65:189–197; Jing, S.

et al. (1992) *Neuron*, 9: 1067–1079) are consistent with the possibility that the trk-docking site of the analogs may be masked upon association of p75 and trkA, but concomitant p75 binding by the analogs could not be formally ruled out.

Analogs C(43–48) and C(44–48) derived from NGF β-turn A'''–B were effective in inhibiting biological assays in PC12 cells without being effective at all in binding assays in E25 cells. The biological effects of C(43–48) must be mediated by the NGF receptor because bFGF was not affected. Perhaps this analog can prevent trkA receptor dimerization, trkA receptor internalization or NGF stability without actually affecting NGF binding. Another explanation is that this inconsistency reflects differences between rat and human trkA receptors which are expressed in neuronal or fibroblastoid cell lines respectively. Inconsistencies between biological and binding responses in transfected fibroblasts versus PC12 cells have been reported (Ip, N.Y. et al. (1993) *Neuron*, 10:137–149). The mechanism of inhibition by NGF β-turn A'''–B analogs will be resolved by further studies.

C–D Region Analogs are Competitive Inhibitors of NGF by Binding trkA Receptors In order to determine the nature of the inhibition of $^{125}$I-NGF binding to trkA receptors by the C–D region analogs, dose response and saturation studies were performed.

Figure 2A:
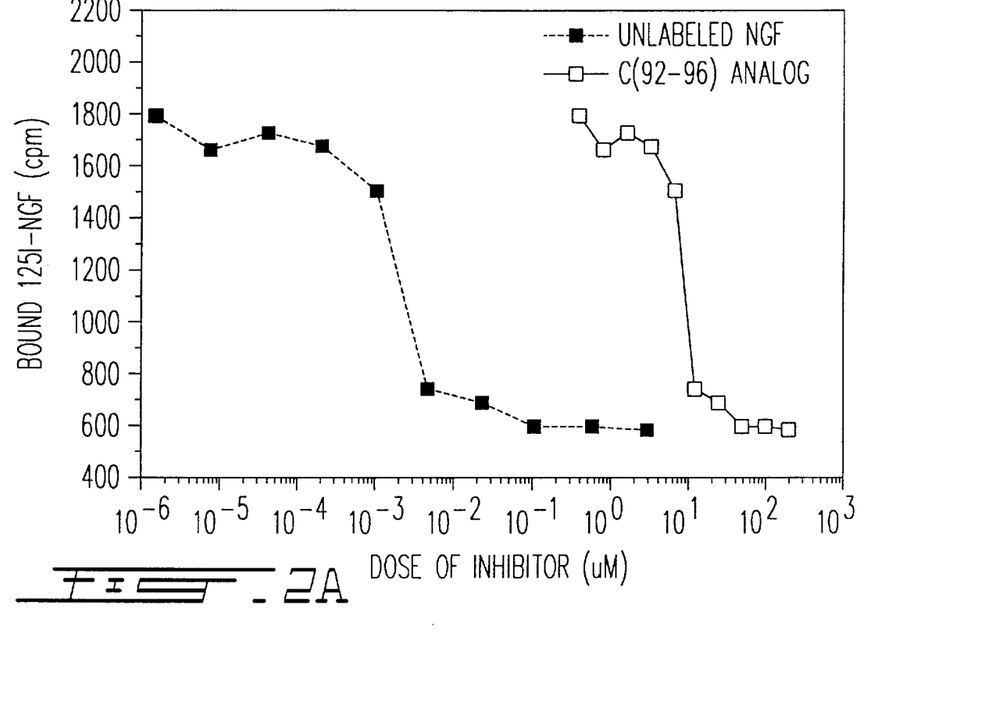
FIGS. 2A–B illustrates the competitive inhibition of $^{125}$I-NGF binding to trka by designed NGF structural analogs in accordance with the present invention.

Dose response studies using increasing amounts of analogs (0.4 μM to 200 μM) or unlabeled NGF (4 nM to 2 μM) were performed in the presence of constant 200 pM concentration of $^{125}$I-NGF (FIG. 2A). Averages of similar experiments showed for analog C(92–96) an $IC_{50}$=23.5±16 μM compared to unlabeled NGF $IC_{50}$=2.65±0.35 nM (FIG. 2B).

Saturation binding assays were performed with trkA receptor expressing E25 cells as described above.

Increasing concentration of inhibitors were tested for their ability to inhibit a constant amount of $^{125}$I-NGF (200 pM)(FIG. 2A). A constant amount of inhibitors (~45 μM of C(92–96) analog, or 2000 fold excess unlabeled NGF) were added to increasing concentrations of $^{125}$I-NGF.

Figure 2B:
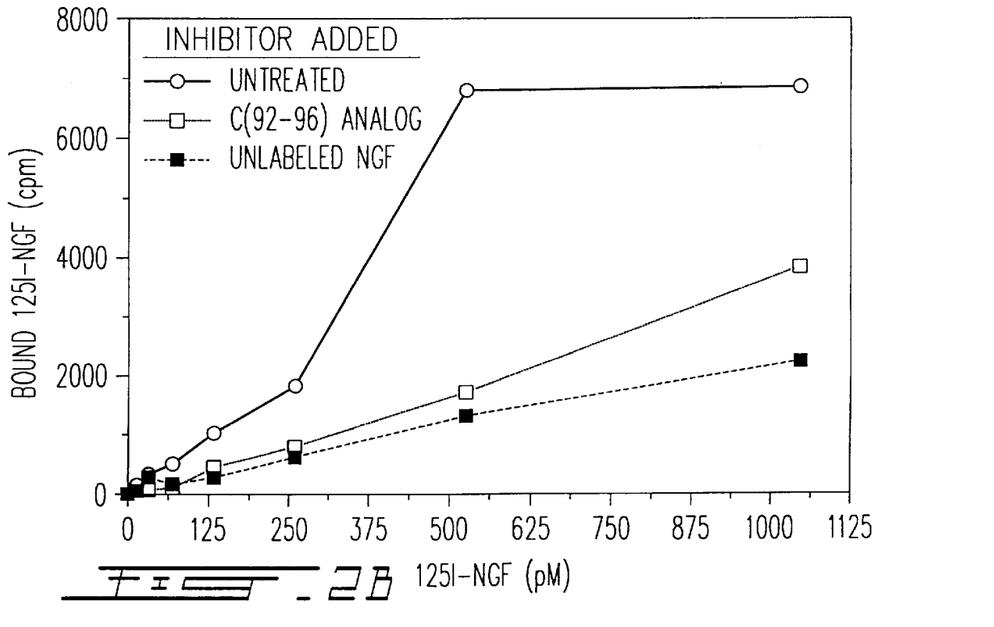

Saturation analysis using increasing concentrations of $^{125}$I-NGF (0–1.13 nM) versus a constant concentration of analog (C(92–96); 45 μM) or a 2,000 fold excess of unlabeled NGF were performed (FIG. 2B). NGF receptor saturation by $^{125}$I-NGF was displaced by both the analog and unlabeled NGF by reducing receptor availability rather than receptor affinity, suggesting that the inhibition is of a competitive nature.

Taken together, these data demonstrate that cyclic sequence analogs of NGF β-turns C–D and A'–A" likely mimic the native architecture and are therefore able to bind to trkA receptors. Secondary structure requirements for antagonistic activity proved to be absolute because linear and random compounds with primary sequences from all β-turns had no effect at the concentrations tested. Thus, the conformation of the analog must retain some if not many of the features found in the original ligand. This experience is emphasized by previous reports of low affinity or inactive linear analogs of NGF (Longo, F. et al. (1990) *Cell Reg.*, 1:189–195; Murphy, R. A. et al. (1993) *J. Neuroscience*, 13(7): 2853–2862).

Analogs derived from β-turn C–D, inhibited neurite outgrowth induced by NGF in PC12 cells, and inhibited NGF binding to several receptor expressing cells. Since all neurotrophins (except NGF) have an extra amino acid in β-turn C–D, binding specificity of NGF for trkA may be partly explained (Ibañez, C. F. et al. (1993) *Eur. Mol. Biol. Org. J.*, 12:2281–2293). This region is likely to confer added specificity to NGF in binding to trkA and perhaps to other neurotrophins in binding to their specific high affinity receptors.

It is unlikely that the mechanism of biological antagonism was to hinder NGF but not bFGF signal transduction because transduction is ras-dependent for both ligands (Kremer, N. E. et al. (1991) *J. Cell Biol.*, 115:809–819). Therefore, the analogs mediate their action by directly binding to the extracellular domain of NGF receptors and in this regard they are different than K252 molecules which mediate their action by inhibition of the kinase activity of trkA (Berg, M. M. et al. (1992) *J. Biol. Chem.*, 267:13–16).

NGF analogs did not behave as agonists of PC12 cells. For agonistic activity the ligand must either engage more than one site on a given receptor, or possess the ability to induce receptor dimerization. Since the analogs are structurally equivalent to only one β-turn region of NGF they would not induce receptor dimerization and would be expected to behave as antagonists in biological assays. Preliminary studies testing combined analogs from NGF β-turns A'–A" and C–D showed additive (but not synergistic) effects in NGF binding assays. It is expected in accordance with the present invention that appropriate coupling of these analogs as homodimers or heterodimers will likely reveal synergy or agonistic function.

Previous studies have implicated the amino terminus of NGF comprising amino acids 1–9 was also implicated in binding to trkA receptors (Kahle, P. et al. (1992) *J. Biol. Chem.*, 267:22707–22710; Ibañez, C. F. et al. (1993) *Eur. Mol. Biol. Org. J.*, 12:2281–2293). However, the amino termini was not resolved crystallographically but is not a β-turn (McDonald, N. Q. et al. (1991) *Nature*, 345: 411–414).

The study of the mechanism of binding by the analogs to trkA only expressing cells versus p75-trkA expressing cells will provide.-more information concerning receptor-ligand interactions. Furthermore, by creating homodimeric and heterodimeric forms of the analogs in accordance with the present invention we will be generating agonistic ligands that permit receptor dimerization.

The present invention will be more readily understood by referring to the following examples which are given to illustrate the invention rather than to limit its scope.

EXAMPLE I

Effect of NGF Analogs in E25 Cell Survival

The inhibitory activity of the compounds of the present invention was tested in more sensitive assays of apoptosis. Cells are dependent on the presence of serum for growth and survival. In the absence of serum (i.e. serum-free media) these cells die (apoptosis) but can be rescued from death with NGF. The peptide analogs can specifically prevent NGF rescue of these cells from death, indicating that they are true NGF antagonists.

Figure 3:
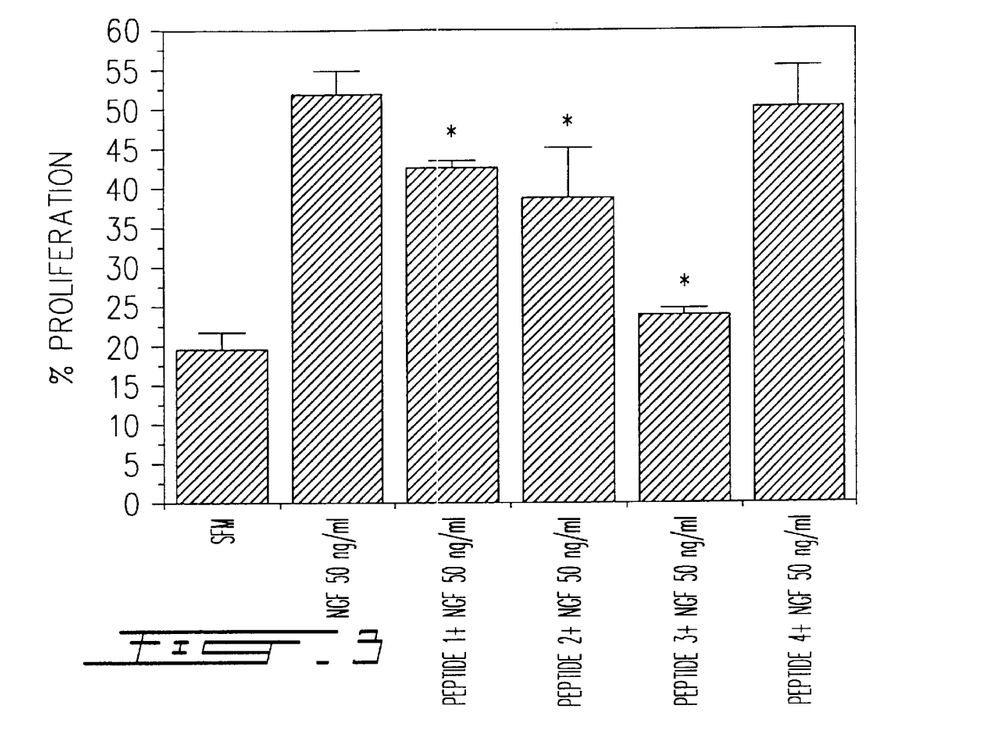
FIG. 3 is a graph which illustrates the inhibition of NGF-induced cell growth or survival by structural analogs.

NGF responsive mouse fibroblasts transfected with human trkA cDNA (E25 cells) were studied. 5,000 E25 cells/well in serum-free media (SFM) were added to 96 well plates (Costar) containing either serum (final concentration 5% FBS), or SFM with serial dilutions of NGF (Prince Labs, Toronto), or the indicated analogs (final concentration 40 ug/ml) in the presence of optimal concentrations of NGF. The proliferative/survival profile of the cells was quantitated using the MTT assay as described over a 36–72 hour period (FIG. 3).

Serum and NGF can rescue SFM induced apoptosis. Addition of certain NGF analogs of the present invention can prevent NGF-mediated rescue, but not serum-mediated rescue an listed in Table IV. Proliferation was calculated as a percent of maximum (serum-induced-100%).

TABLE IV

| | Sequence | Code | SEQ ID NO: |
|---|---|---|---|
| Peptide 1 = | Fmoc-YCTDEKQCY-OH | C(92–95) | SEQ ID NO: 22 |
| Peptide 2 = | Acetyl-YCTDEKQCY-OH | C(92–96) | SEQ ID NO: 22 |
| Peptide 3 = | Fmoc-YCDIKGKECY-OH | C(30–35) | SEQ ID NO: 2 |
| Peptide 4 = | Acetyl-YCDIKGKECY-OH | C(30–35) | SEQ ID NO: 2 |

FIG. 3 is a graph which illustrates the assays results indicated significant differances from NGF treated cells.

The NGF antagonistic activity of the analogs further indicates that they are structural analogs of NGF. The importance of these assays is two fold. First, the analogs were effective in bioassays using cells other than PC12 cells, expanding the types of tissues tested. Second, it is shown that lack of NGF availability, due to antagonistic activity of the analogs, can induce an active process of cell death (apoptosis). This antagonism may be desired in cases of neuromas at the end of an amputated limb.

Effect of NGF Analogs on trkA Receptor Internalization

Some of the peptide analogs are shown to induce internalization of the trkA receptor, which may be one mechanism of downmodulation of receptor.

E25 single cell suspensions were first treated with NGF analog C(92–97) (Fmoc-YCTDEKQACY-OH) (10 μM) or with NGF (2 nM) using conditions which allow ligand-induced induced internalization of surface receptors (37° C., in culture media), or conditions which do not allow internalization (4° C., 0.05% sodium azide) for 30 min. Expression of surface trkA receptors was quantified by FACScan analysis.

Figure 4A:
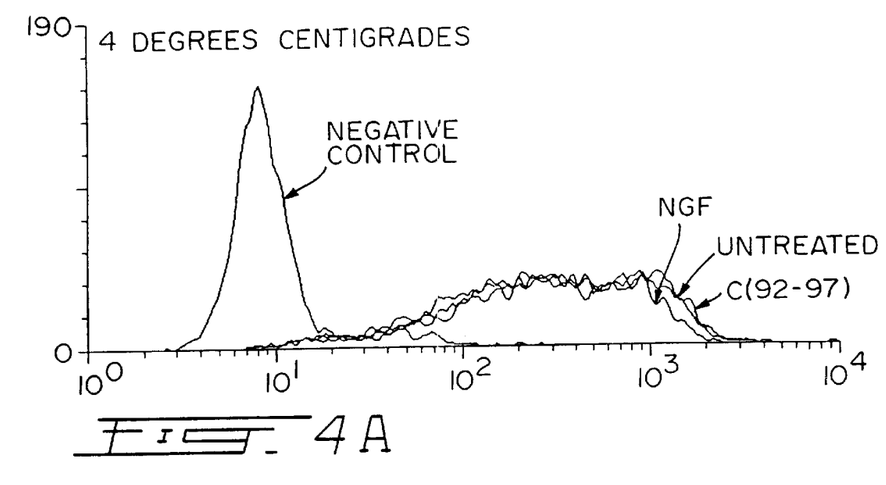
FIGS. 4A–B illustrates FACScan profiles of surface p14 trkA using an anti-trkA specific monoclonal antibody, after binding of structural analogs under different conditions.

FIG. 4A illustrates FACScan profiles using an anti-trkA specific monoclonal antibody versus control mouse IgG.

Figure 4B:
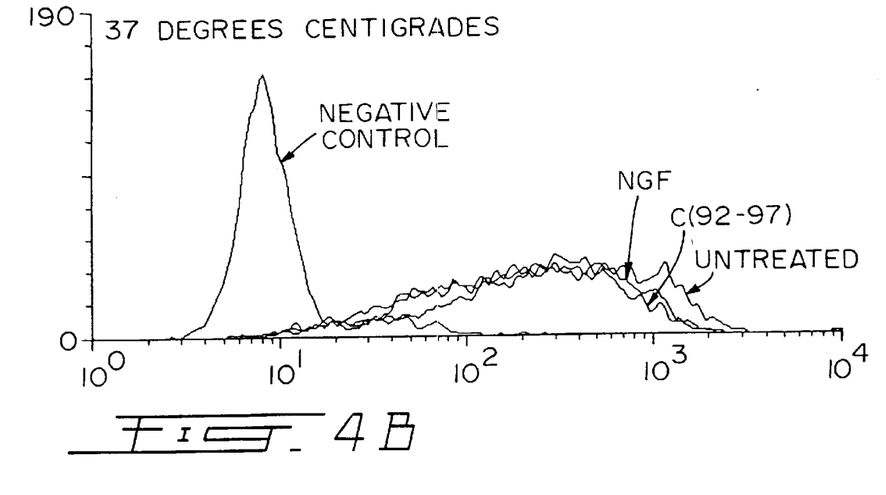
Figure 4C:
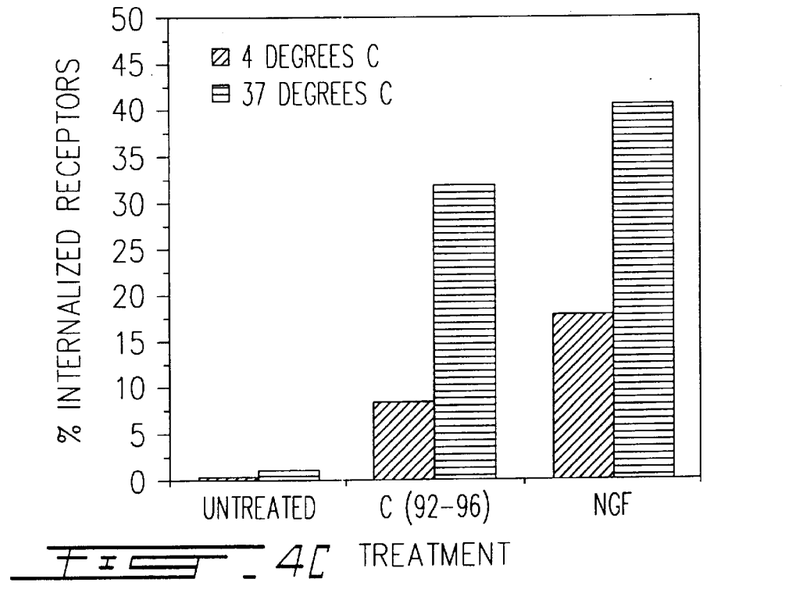
FIG. 4C is a graph of the analysis of the % reduction of cell surface mean fluorescence channel after receptor internalization.

FIG. 4B is a graph of the analysis of the % reduction of cell surface mean fluorescence channel (MFC, using the Lysis (B.D.) software) after receptor internalization.

NGF and the structural NGF analog C(92–97) induced the disappearance of surface trkA receptors at the permissive conditions only, indicating ligand-induced receptor internalization.

Induced internalization of receptors by their ligands at 37° C. (permissive conditions) is a well-known process. Internalization requires receptor association with cytoskeletal structures, and clathrin-coated vesicles upon ligand binding (Corvera, S. et al. (1989) *J. Biol. Chem.*, 264:12568–12572). The ability of the analogs to induce internalization is strong evidence of their binding to NGF receptors and inducing biophysical changes in the receptor and biological changes in the cell.

Ligands are internalized together with the receptors. This knowledge is useful two fold. First, analogs which are coupled to a toxin can be internalized into a receptor-expressing tumor cell whereby the toxin would then destroy the tumor cell. Second, receptor internalization is a means to temporarily downmodulate receptor expression or responses to a ligand.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound that inhibits or mimics the biological activity of a neurotrophin, said compound having
   a cyclic structure and
   a disulfide bridge
   wherein said compound binds to at least one neurotrophin receptor and comprises a peptide selected from the group consisting of:
   Z-X C K G K E C X; SEQ ID NO:1
   Z-X C D I K G K E C X; SEQ ID NO:2
   Z-X C T A I K G K E C X; SEQ ID NO:3
   Z-X C I K G K E C X; SEQ ID NO:4
   Z-X C I N N S V C X; SEQ ID NO:7
   Z-X C N I N N S V C X; SEQ ID NO:8
   Z-X C N I N N S C X; SEQ ID NO:9
   Z-X C S N P V E S C X; SEQ ID NO:12
Z-X C A S N P V E S C X; SEQ ID NO:13
X C A S N P V E C; SEQ ID NO:14
X C A S N P V E C X; SEQ ID NO:15
Z-X C T D E K Q C X; SEQ ID NO:18 and
Z-X C T D E K Q A C X; SEQ ID NO:19 wherein,

X is any uncharged amino acid or hydropathic amino acid; and

Z is absent or a protective group selected from the group consisting of Fmoc group and acetyl groups.

2. The compound of claim 1, wherein the neurotrophin is selected from the group consisting of NGF, BDNF, NT3, and NT-4/5.

3. The compound of claim 1, wherein the neurotrophin receptor is selected from the group consisting of trkA, trkB trkC, trkE, and p75.

4. The compound of claim 3, wherein said neurotrophin is NGF.

5. A composition comprising a compound as defined in claim 1 in association with a carrier.

* * * * *

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
          (A) LENGTH: 8 amino acids
          (B) TYPE: amino acid
          (C) STRANDEDNESS: single
          (D) TOPOLOGY: linear      (ii) MOLECULE TYPE: peptide      (ix) FEATURE:
          (A) NAME/KEY: Modified-site
          (B) LOCATION: one-of (1, 8)
          (D) OTHER INFORMATION: /note= "Xaa is any uncharged amino acid
              or hydropathic amino acid"

(xi) SEQUENCE DESCRIPTION: SEQ ID NO: 1:

Xaa Cys Lys Gly Lys Glu Cys Xaa
1            5

(2) INFORMATION FOR SEQ ID NO: 2:

```
     (i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: one-of (1, 10)
         (D) OTHER INFORMATION: /note= "Xaa is any uncharged amino acid
             or hydropathic amino acid"

(xi) SEQUENCE DESCRIPTION: SEQ ID NO: 2:

Xaa Cys Asp Ile Lys Gly Lys Glu Cys Xaa
1               5                  10

(2) INFORMATION FOR SEQ ID NO: 3:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: one-of (1, 11)
         (D) OTHER INFORMATION: /note= "Xaa is any uncharged amino acid
             or hydropathic amino acid"

(xi) SEQUENCE DESCRIPTION: SEQ ID NO: 3:

Xaa Cys Thr Ala Ile Lys Gly Lys Glu Cys Xaa
1               5                  10

(2) INFORMATION FOR SEQ ID NO: 4:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION: one-of (1, 9)
         (D) OTHER INFORMATION: /note= "Xaa is any uncharged amino acid
             or hydropathic amino acid"

(xi) SEQUENCE DESCRIPTION: SEQ ID NO: 4:

Xaa Cys Ile Lys Gly Lys Glu Cys Xaa
1               5

(2) INFORMATION FOR SEQ ID NO: 5:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 5:

Ala Thr Asp Ile Lys Gly Lys Glu Val
1               5
```

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 6:

```
Thr Ile Gly Glu Ala Asp Lys Lys Val
 1               5
```

(2) INFORMATION FOR SEQ ID NO: 7:

(i) SEQUENCE CHARACTERISTICS:
        (A) LENGTH: 9 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Modified-site
        (B) LOCATION: one-of (1, 9)
        (D) OTHER INFORMATION: /note= "Xaa is any uncharged amino acid
            or hydropathic amino acid"

(xi) SEQUENCE DESCRIPTION: SEQ ID NO: 7:

```
Xaa Cys Ile Asn Asn Ser Val Cys Xaa
 1               5
```

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Modified-site
        (B) LOCATION: one-of (1, 10)
        (D) OTHER INFORMATION: /note= "Xaa is any uncharged amino acid
            or hydropathic amino acid"

(xi) SEQUENCE DESCRIPTION: SEQ ID NO: 8:

```
Xaa Cys Asn Ile Asn Asn Ser Val Cys Xaa
 1               5                  10
```

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Modified-site
        (B) LOCATION: one-of (1, 9)
        (D) OTHER INFORMATION: /note= "Xaa is any uncharged amino acid
            or hydropathic amino acid"

(xi) SEQUENCE DESCRIPTION: SEQ ID NO: 9:

```
Xaa Cys Asn Ile Asn Asn Ser Cys Xaa
```

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 10:

```
Val Asn Ile Asn Asn Ser Val Phe
1               5
```

(2) INFORMATION FOR SEQ ID NO: 11:

(i) SEQUENCE CHARACTERISTICS:
        (A) LENGTH: 8 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 11:

```
Asn Asn Ser Phe Val Ile Asn Val
1               5
```

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Modified-site
        (B) LOCATION: one-of (1, 10)
        (D) OTHER INFORMATION: /note= "Xaa is any uncharged amino acid
            or hydropathic amino acid"

(xi) SEQUENCE DESCRIPTION: SEQ ID NO: 12:

```
Xaa Cys Ser Asn Pro Val Glu Ser Cys Xaa
1               5                   10
```

(2) INFORMATION FOR SEQ ID NO: 13:

(i) SEQUENCE CHARACTERISTICS:
        (A) LENGTH: 11 amino acids
        (B) TYPE: amino acid
        (C) STRANDEDNESS: single
        (D) TOPOLOGY: linear     (ii) MOLECULE TYPE: peptide     (ix) FEATURE:
        (A) NAME/KEY: Modified-site
        (B) LOCATION: one-of (1, 11)
        (D) OTHER INFORMATION: /note= "Xaa is any uncharged amino acid
            or hydropathic amino acid"

(xi) SEQUENCE DESCRIPTION: SEQ ID NO: 13:

```
Xaa Cys Ala Ser Asn Pro Val Glu Ser Cys Xaa
1               5                   10
```

(2) INFORMATION FOR SEQ ID NO: 14:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa is any uncharged amino acid
                or hydropathic amino acid"

(xi) SEQUENCE DESCRIPTION: SEQ ID NO: 14:

Xaa Cys Ala Ser Asn Pro Val Glu Cys
1               5

(2) INFORMATION FOR SEQ ID NO: 15:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: one-of (1, 10)
            (D) OTHER INFORMATION: /note= "Xaa is any uncharged amino acid
                or hydropathic amino acid"

(xi) SEQUENCE DESCRIPTION: SEQ ID NO: 15:

Xaa Cys Ala Ser Asn Pro Val Glu Cys Xaa
1               5                   10

(2) INFORMATION FOR SEQ ID NO: 16:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 16:

Arg Ala Ser Asn Pro Val Glu Ser Gly
1               5

(2) INFORMATION FOR SEQ ID NO: 17:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 17:

Ala Asn Val Ser Arg Ser Pro Glu Gly
1               5

(2) INFORMATION FOR SEQ ID NO: 18:

(i) SEQUENCE CHARACTERISTICS:
            (A) LENGTH: 9 amino acids
            (B) TYPE: amino acid (C) STRANDEDNESS: single
            (D) TOPOLOGY: linear (ii) MOLECULE TYPE: peptide (ix) FEATURE:
            (A) NAME/KEY: Modified-site
            (B) LOCATION: one-of (1, 9)
            (D) OTHER INFORMATION: /note= "Xaa is any uncharged amino acid
                or hydropathic amino acid"

(xi) SEQUENCE DESCRIPTION: SEQ ID NO: 18:

Xaa Cys Thr Asp Glu Lys Gln Cys Xaa
1               5

(2) INFORMATION FOR SEQ ID NO: 19:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: one-of (1, 10)
            (D) OTHER INFORMATION: /note= "Xaa is any uncharged amino acid
                or hydropathic amino acid"

(xi) SEQUENCE DESCRIPTION: SEQ ID NO: 19:

Xaa Cys Thr Asp Glu Lys Gln Ala Cys Xaa
1               5                   10

(2) INFORMATION FOR SEQ ID NO: 20:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 20:

Thr Thr Asp Glu Lys Gln Ala Ala Trp
1               5

(2) INFORMATION FOR SEQ ID NO: 21:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 21:

Thr Glu Gln Ala Thr Asp Lys Ala Trp
1               5

(2) INFORMATION FOR SEQ ID NO: 22:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide -continued (xi) SEQUENCE DESCRIPTION: SEQ ID NO: 22:

Tyr Cys Thr Asp Glu Lys Gln Cys Tyr
1               5

(2) INFORMATION FOR SEQ ID NO: 23:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 23:

His Cys Thr Asp Glu Lys Gln Cys His
1               5